(12) United States Patent
Ogawa et al.

(10) Patent No.: US 8,514,403 B2
(45) Date of Patent: Aug. 20, 2013

(54) SAMPLE ANALYSIS METHOD

(75) Inventors: Yuichi Ogawa, Aoba-Ku (JP);
Shinichiro Hayashi, Miyagi (JP); Seiji Kamba, Nagaokakyo (JP); Takashi Kondo, Nagaokakyo (JP)

(73) Assignees: Tohoku University, Miyagi (JP); Murata Manufacturing Co., Ltd., Nagaokakyo-Shi (JP)

( * ) Notice: Subject to any disclaimer, the term of this patent is extended or adjusted under 35 U.S.C. 154(b) by 0 days.

(21) Appl. No.: 13/086,759

(22) Filed: Apr. 14, 2011

(65) Prior Publication Data

US 2011/0205528 A1   Aug. 25, 2011

Related U.S. Application Data

(63) Continuation of application No. PCT/JP2009/004735, filed on Sep. 18, 2009.

(30) Foreign Application Priority Data

Oct. 24, 2008   (JP) .................................. 2008-265415

(51) Int. Cl.
*G01B 11/02*   (2006.01)
(52) U.S. Cl.
USPC ........................................................... 356/496
(58) Field of Classification Search
USPC ........................................................... 356/496
See application file for complete search history.

(56) References Cited

U.S. PATENT DOCUMENTS

| 6,954,309 | B2 * | 10/2005 | Knobloch et al. | ............ 359/586 |
| 7,326,930 | B2 * | 2/2008 | Crawely | ..................... 250/341.1 |
| 7,701,587 | B2 * | 4/2010 | Shioda et al. | ................. 356/486 |
| 2005/0087690 | A1 | 4/2005 | Usami et al. | |
| 2007/0229094 | A1 | 10/2007 | Kasai et al. | |

FOREIGN PATENT DOCUMENTS

| JP | 2004101510 A | 4/2004 |
| JP | 2004198250 A | 7/2004 |
| JP | 2007192607 A | 8/2007 |
| JP | 2008083020 A | 4/2008 |
| JP | 2008175794 A | 7/2008 |
| WO | WO-03-058212 A1 | 7/2003 |
| WO | WO-2006030756 A1 | 3/2006 |

OTHER PUBLICATIONS

"Applications of Terahertz Time-Domain Reflectometry"; H. Kitahara, K. Takano, T. Ikeda, M. Tani, and M. Hangyo; IEEJ Transactions on Fundamentals and Materials; vol. 127, No. 7, 2007, pp. 391-396.
International Search Report, mailed Oct. 20, 2009.

\* cited by examiner

Primary Examiner — Tarifur Chowdhury
Assistant Examiner — Jonathon Cook
(74) Attorney, Agent, or Firm — Dickstein Shapiro LLP

(57) ABSTRACT

A sample analysis method is provided for analyzing a sample having a permeability to terahertz radiation and accurately measure the composition, physical properties, mass and dimensions of a very small sample or a minute amount of sample by irradiating the sample with terahertz radiation. In the method, a reflective member is provided adjoining a first principal surface of the sample, an entrance member is provided adjoining a second principal surface of the sample, terahertz radiation is delivered from outside of entrance member towards the sample, and the sample is analyzed using an interference wave generated from a first-surface reflected wave at the interface between the first principal surface of the sample and the reflective member and a second-surface reflected wave at the interface between the second principal surface of the sample and the entrance member.

16 Claims, 9 Drawing Sheets

SAMPLE ANALYSIS METHOD

This is a continuation of application Serial No. PCT/JP2009/004735, filed Sep. 18, 2009, the entire contents of which is hereby incorporated by reference.

TECHNICAL FIELD

This invention relates to techniques for analyzing a sample using terahertz radiation. Terahertz radiation refers to electromagnetic radiation having frequencies ranging from 20 GHz to 120 THz. Examples of such an analysis include measuring the physical properties and dimensions of a sample itself and measuring the amount of biopolymer adhering to the sample.

BACKGROUND ART

When a sample to be measured is irradiated with terahertz radiation, a measurement result according to the physical properties of the sample can be obtained. For example, when the sample is irradiated with terahertz radiation having different wavelengths, terahertz waves having specific wavelengths are absorbed in the sample by electromagnetic radiation absorption of the sample. Therefore, the terahertz radiation transmittance versus frequency characteristic emerges in a specific waveform according to the physical properties of the sample.

A known method for measuring the terahertz radiation transmittance is terahertz time-domain spectroscopy (hereinafter, referred to as THz-TDS). Example 2 in Patent Literature 1 discloses a THz-TDS method using a reflecting optical system. In this example, the terahertz radiation emitted from a terahertz radiation generator is focused through parabolic mirrors onto the sample, and the terahertz radiation reflected on the sample is then focused to a terahertz radiation detector using parabolic mirrors.

Patent Literature 1: Published Japanese Patent Application No. 2008-83020

SUMMARY OF INVENTION

Technical Problem

A conventional sample holder and a terahertz wave propagation path is shown in FIG. 11. It is to be noted that FIG. 11 was made by the applicant based on the description in Patent Literature 1.

As shown in FIG. 11, the conventional sample holder 100 is composed of a sample 102 as an object to be measured, and a metal film 101 adjoined to the sample 102. The metal film 101 is a mirror that can reflect approximately 100% of the terahertz radiation.

In order to measure the terahertz radiation transmittance of the sample 102, the sample 102 is irradiated with terahertz radiation. The terahertz wave propagation path inside the sample at this time is explained with reference to FIG. 11.

First, the sample 102 is irradiated with an irradiation beam I which is terahertz radiation. A part of the irradiation beam I directly hits the sample 12 and is reflected as a reflected wave $R_0$, while the remaining part thereof becomes an intra-sample propagating wave $r_0$ travelling inside the sample 102. At this time, a difference in dielectric constant between the atmosphere and the sample 102 causes refractions in the reflected wave $R_0$ and the intra-sample propagating wave $r_0$. The intra-sample propagating wave $r_0$ is reflected on the metal film 101 as intra-sample propagating wave $r_1$, a part of the intra-sample propagating wave $r_1$ is reflected at the interface between the sample 102 and the atmosphere as intra-sample propagating wave $r_2$, and the remaining part thereof is emitted through the interface from the sample 102 into an outgoing wave $R_1$.

The magnitudes of the amplitudes of the reflected wave $R_0$ and outgoing wave $R_1$ in this case are determined versus time and Fourier transformed, thereby obtaining the composition, physical properties and mass of the sample 102. This is an existing THz-TDS method.

This conventional THz-TDS method, however, has the following problems.

One problem is that the absorption of terahertz radiation inside the sample is not adequately achieved and, therefore, the amplitude difference between the reflected wave $R_0$ and the outgoing wave $R_1$ does not significantly vary regardless of the presence or absence of the sample, which prevents an adequate analysis of the sample 102. In particular, the terahertz wave propagation path itself is very short if the sample 102 is very small or very thin, which may result in inadequate electromagnetic radiation absorption. In addition, electromagnetic radiation absorption becomes inadequate if the amount of substance to be measured contained in the sample 102 is minute. Therefore, the measurement of a minute sample amount of 1 mg or below cannot be achieved by the conventional method.

A further problem is that if the entire surface of the sample 102 is analyzed by scanning the sample 102 in the direction along the surface, great irregularities in the sample surface may cause the angles of the reflected wave and outgoing wave from the sample 102 to become unstable and thereby prevent accurate measurement of the angles.

A challenge to be solved by the present invention is to accurately measure the composition, physical properties, mass and dimensions of very small samples, minute amounts of samples or thin-layer samples.

Solution to Problem

A sample analysis method according to the present invention is a method for analyzing a sample having a permeability to terahertz radiation, the method including the steps of: providing a reflective member adjoining a first principal surface of the sample; providing an entrance member adjoining a second principal surface of the sample; delivering terahertz radiation from the outside of the entrance member towards the sample; and analyzing the sample using an interference wave generated from a first-surface reflected wave at the interface between the first principal surface of the sample and the reflective member and a second-surface reflected wave at the interface between the second principal surface of the sample and the entrance member. Terahertz radiation refers to electromagnetic radiation having frequencies ranging from 20 GHz to 120 THz.

In a particular embodiment of the present invention, the interface between the first principal surface of the sample and the reflective member and the interface between the second principal surface of the sample and the entrance member are parallel to each other.

In another particular embodiment of the present invention, the interference wave is generated from an outgoing wave obtained by the first-surface reflected wave having passed through the sample and the entrance member and emitted from the entrance member, and an outgoing wave obtained by the second-surface reflected wave having passed through and emitted from the entrance member.

In still another particular embodiment of the present invention, the interference wave is generated from a multi-reflection wave obtained by multiple reflections of a terahertz wave at the interface between the first principal surface of the sample and the reflective member, and a multi-reflection wave obtained by multiple reflections of a terahertz wave at the interface between the second principal surface of the sample and the entrance member. The multi-reflection wave refers to a wave reflected multiple times at each of the interface between the sample and the reflective member, and the interface between the sample and the entrance member in the process from the irradiation of terahertz radiation towards the sample to the emission from the sample.

In still another embodiment of the present invention, the refractive index of the reflective member is greater than that of the sample, the refractive index of the entrance member is greater than that of the sample, and the refractive index of the entrance member is greater than that of the air present outside the entrance member.

In still another embodiment of the present invention, a terahertz radiation reflection suppression layer is provided adjoining and outside the entrance member.

In still another embodiment of the present invention, the sample analysis method is a method in which the sample is formed of a plurality of layers of different dielectric constants, and the sample is analyzed in the layer of the plurality of layers in the sample which is adjoined to the reflective member.

In still another embodiment of the present invention, a sample analysis method for analyzing a sample having a permeability to terahertz radiation includes the steps of: providing a reflective member adjoining a first principal surface of the sample; providing an entrance member adjoining a second principal surface of the sample; delivering terahertz radiation from the outside of the entrance member towards the sample, thereby generating a reflected wave at the interface between the first principal surface of the sample and the reflective member, a reflected wave at the interface between the second principal surface of the sample and the entrance member, and a reflected wave at the interface between the entrance member and the outside of the entrance member; and then analyzing the sample using an interference wave generated from a plurality of outgoing waves finally emitted outside through the entrance member. The outgoing waves finally emitted outside refer to terahertz waves emitted outside after having been propagated one or more times inside the sample and/or the entrance member.

Advantageous Effects of Invention

According to the sample analysis method of the present invention, the composition, physical properties, mass and dimensions of a very small sample, a minute amount of sample or a thin-layer sample can be accurately measured.

DESCRIPTION OF EMBODIMENTS

An embodiment of the present invention will be now described focusing on major differences from the conventional technique. Such differences from the conventional technique include sample holder 10 and terahertz wave propagation paths inside the sample holder. It is to be noted that a light source of terahertz radiation, an optical system, a data processing method and the like will be specifically described in Examples below.

Figure 1:
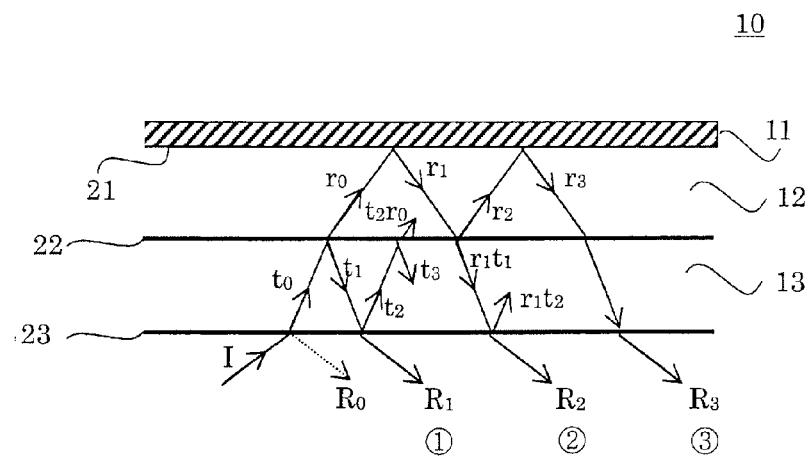
FIG. 1 is a view showing a sample holder according to an embodiment and terahertz wave propagation paths in the sample holder. The circled numbers correspond to the circled numbers is FIG. 4(*a*).

With reference to FIG. 1, a description is now given of the sample holder 10 in this embodiment and the terahertz wave propagation paths inside the sample holder. The sample holder 10 in this embodiment is composed of a sample 12 as the object to be measured, a reflective member 11 adjoined to one of two principal surfaces of the sample 12, and an entrance member 13 adjoined to the other principal surface of the sample 12.

The reflective member 11 is a mirror that has a greater refractive index than the sample 12 and can reflect approximately 100% of terahertz radiation. Other reflective members that can be used include members having negative refractive indices, such as metamaterials.

The entrance member 13 is made of a material having a refractive index different from that of the sample 12 and greater than that of the air. More preferably, the refractive index of the entrance member 13 is greater than that of the sample 12. For example, high-resistance silicon (Si) or light-transmissive ceramics can be as materials for the entrance member 13. The reason for this is that multiple reflections described later can be effectively used in these materials.

The sample 12 is a material having permeability to and absorbability of terahertz radiation.

Hereinafter, the boundary between the reflective member 11 and the sample 12 is referred to as a first interface 21, the boundary between the sample 12 and the entrance member 13 is referred to as a second interface 22, and the boundary between the entrance member 13 and the atmosphere is referred to as a third interface 23. Furthermore, the reflected wave generated at the first interface 21 is referred to as a first-surface reflected wave, the reflected wave generated at the second interface 22 is referred to as a second-surface reflected wave, and the reflected wave generated at the third interface 23 is referred to as a third-surface reflected wave.

The present invention is characterized in that the sample 12 is analyzed using an interference wave generated from the first-surface reflected wave which is generated at the first interface 21 and the second-surface reflected wave which is generated at the second interface 22. Hereinafter, the analysis will be described.

First, terahertz radiation is delivered from the outside of the entrance member 13 (the atmosphere side) towards the sample holder 10. This irradiation beam I passes through the third interface 23 into an intra-entrance member propagating wave $t_0$. At this time, a difference in dielectric constant between the atmosphere and the entrance member 13 results in refraction of the terahertz wave. A part of the intra-entrance member propagating wave $t_0$ enters the sample 12, while the remaining part thereof is reflected at the second interface 22 into an intra-entrance member propagating wave $t_1$ (reflected wave). A part of the intra-entrance member propagating wave $t_1$ is reflected at the third interface 23 into an intra-entrance member propagating wave $t_2$ (reflected wave), while the remaining part thereof passes through the third interface 23 and is emitted as an outgoing wave $R_1$.

The propagating wave having entered the sample 12 propagates as an intra-sample propagating wave $r_0$ through the sample at a predetermined angle. The predetermined angle is determined by the difference in dielectric constant between the entrance member 13 and the sample 12. A first part intra-sample propagating wave $r_0$ is reflected at the first interface 21 into an intra-sample propagating wave $r_1$ (reflected wave). Furthermore, a second part of the intra-sample propagating wave $r_1$ is reflected at the second interface 22, while the remaining part thereof passes through the second interface 22 and then through the third interface 23 and is emitted as an outgoing wave $R_2$. The wave having not passed through but reflected at the third interface 23 becomes an intra-entrance member propagating wave $r_1 t_2$ (reflected wave).

The propagating wave that is a part of the intra-sample propagating wave $r_1$ reflected at the second interface 22 becomes an intra-sample propagating wave $r_2$. The intra-sample propagating wave $r_2$ is reflected at the first interface 21, a part thereof then passes through the second interface 22, and a part of the wave having passed through the second interface 22 then passes through the third interface 23 and is emitted as another outgoing wave $R_3$.

The composition, physical properties, mass and dimensions of the sample 12 can be obtained by determining the magnitude of the amplitude of an interference wave generated from the outgoing wave $R_1$ and outgoing wave $R_2$ as a function of time and Fourier transforming it. Furthermore, the magnitude of the amplitude of an interference wave generated from the outgoing wave $R_1$, outgoing wave $R_2$ and outgoing wave $R_3$ can be determined as a function of time and Fourier transformed. Moreover, if the magnitude of the amplitude of an interference wave formed by multiple reflections at the first interface 21, the second interface 22 and the third interface 23 is determined as a function of time and Fourier transformed, the composition, physical properties, mass and dimensions of the sample 12 can be obtained with higher accuracy.

Figure 11:
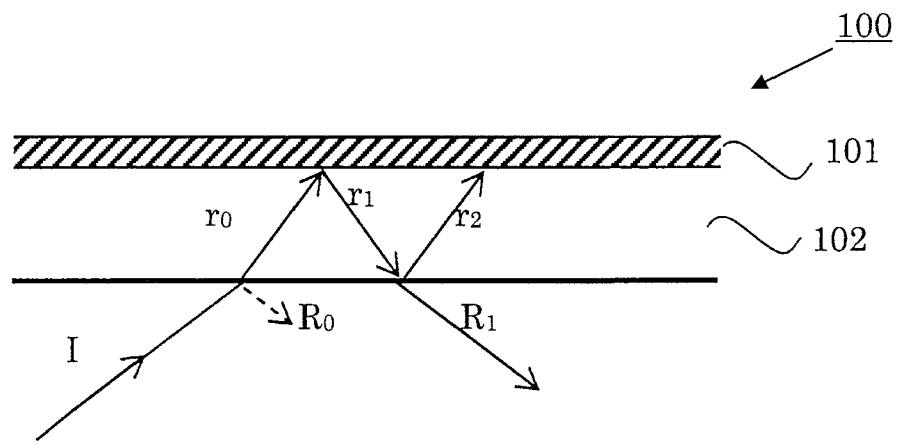
FIG. 11 is a view illustrating a sample holder and a terahertz wave propagation path in a conventional THz-TDS method.

The conventional THz-TDS technique has a problem that if the sample is scanned in the in-plane direction for multi-point measurement, any great irregularities in the sample surface cause the angles of the reflected wave $R_0$ and outgoing wave $R_1$ ($R_0$ and $R_1$ in FIG. 11) from the sample 102 to become unstable and thereby prevent accurate measurement of the angles.

In contrast, the present invention has an advantage that since, as shown in FIG. 1, a smooth entrance member 13 is provided in the sample holder 10, and the angles of the reflected waves from the second interface 22 can be stably measured. Furthermore, the present invention has another advantage that since the smooth entrance member 13 is provided in the sample holder 10 and the distance between the second interface 22 and a detecting element 36 is kept constant, the reflected waves from the second interface 22, in a multi-point measurement by scanning of the sample in the in-plane direction, can be measured on the same time base. Therefore, the physical properties and the like of the sample 12 can accurately be measured.

The conventional THz-TDS technique has another problem that if the sample 102 is very small or very thin, the terahertz wave propagation path itself inside the sample is very short, and this may result in inadequate electromagnetic radiation absorption and prevent accurate measurement. The conventional technique has still another problem that if the amount of substance to be measured contained in the sample 102 is minute, the electromagnetic radiation absorption becomes inadequate, thereby preventing accurate measurement.

In contrast, since multiple reflections of terahertz waves at the second interface and first interface are actively used according to the present invention, the terahertz wave propagation path can be substantially elongated, which enables measurement of even very small samples or minute amounts of samples.

In the conventional THz-TDS technique, the surface of the sample 102 is brought into contact with the atmosphere before the sample 102 is set in a measurement device. During that period, impurities in the atmosphere adhere to the sample 102, which prevents accurate measurement. In contrast, the sample 12 is sandwiched between the reflective member 11 and the entrance member 13 in the present invention. This avoids the direct contact of the sample with the atmosphere and solves the problem of adhesion of impurities to the sample.

Now, the attenuated total reflection (ATR) method is taken as a comparative example and comparison is made between the comparative example and the present invention.

The ATR method is an infrared spectrometry method using infrared light. In this method, as shown in FIG. 12, a sample 202 and a silicon (Si) prism 203 having a greater refractive index than the sample are brought into contact with each other, the angle of incidence of an infrared light irradiation beam I is adjusted to cause total reflection inside the prism and an outgoing wave $R_1$ is measured.

In this case, the infrared light enters the sample 202 slightly, to a predetermined depth, and then reflects from the sample 202. Thus, infrared absorption spectra on the surface of the sample 202 can be obtained. Analyzing the obtained spectra leads to the structural analysis and qualitative and quantitative analyses of the sample 202. The ATR method is characterized by the use of such evanescent waves E entering the sample 202 to a predetermined depth in the above manner.

Figure 12:
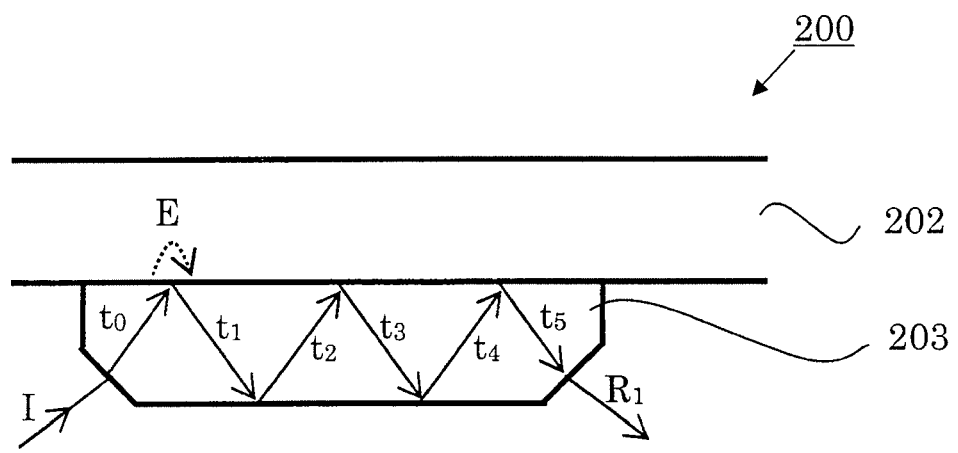
FIG. 12 is a view showing a sample holder and a terahertz wave propagation path in the ATR method as a comparative example.

Furthermore, the number of samplings of the sample 202 in the ATR method using multiple reflections inside the prism as shown in FIG. 12 is the number of reflections which depend on the length and thickness of the prism 203 and the angle of incidence of the irradiation beam I emitted from a light source.

The invention method is different from the ATR method in the following respects. Although the ATR method and the invention method are the similar in the use of multiple reflections of terahertz waves, the methods differ in principle in that the ATR method uses multiple reflections generated in the prism 203 by causing total reflection at the outside surface of the sample 202, while the invention method additionally uses multiple reflections generated inside the sample.

The method using electromagnetic radiation absorption inside the sample is more likely to cause electromagnetic radiation absorption and is therefore more suitable for detection of very small samples 12 and minute amounts of samples 12 than the ATR method using electromagnetic radiation absorption at the sample surface.

Furthermore, since the ATR method uses multiple reflections inside the entrance member (prism), rather than multiple reflections inside the sample, it is not suitable for measurement of samples transmitting terahertz radiation. In contrast, the method of the invention is suitable for samples transmitting terahertz radiation and fully differs from the ATR method by the use of multiple reflections inside the sample.

The present invention is greatly different in the above respects from the conventional technique. Hereinafter, examples of the present invention will be specifically described with reference to the drawings.

EXAMPLE 1

Figure 2:
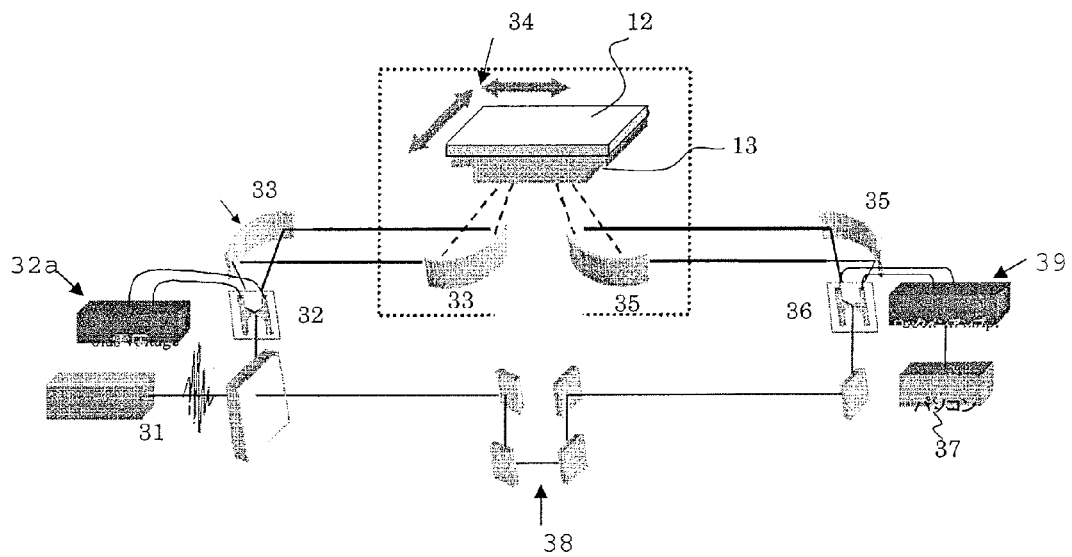
FIG. 2 is a diagram showing the whole of a THz-TDS imaging system in Example 1.

FIG. 2 is an imaging system 30 using terahertz time-domain spectroscopy (THz-TDS). The imaging system 30 is configured to place an XY stage 34 for moving a sample in the optical path for THz-TDS to allow an image of the sample 12 to be captured by raster scanning the sample 12, whereby transmittance images and absorbance images at different frequencies can be obtained.

Terahertz radiation is output by generating an instantaneous current by means of a photocarrier produced by applying light of a femtosecond pulse laser to a photoconductive switch or antenna (generating element) 32 to which a bias voltage from source 32a is applied, and thereby producing terahertz pulse radiation proportional to the temporal differentiation of the generated current. On the other hand, a photoconductive switch or antenna (detecting element) 36 for terahertz radiation has an opposite construction to the photoconductive switch 32 and an ammeter is connected thereto instead of applying voltage. It can be connected to an amplifier 39, which is in turn connected to a computer 37. Elements 33 and 35 are off-axis parabolic mirrors.

When, a photocarrier is produced by irradiating the gap in the detecting antenna 36 with light from the femtosecond laser, the electrical conductivity of the gap region increases, and the antenna circuit is temporarily closed. If a terahertz wave reaches the detecting element 36 at this time, the electric field of the terahertz wave is applied to the detecting element 36 to cause a current proportional to the amplitude of the terahertz wave to flow through the antenna circuit, whereby the value of the current can be detected by the ammeter.

In addition, by applying an optical delay 38 between the light from the femtosecond laser (probe light) and the terahertz wave, the electric field intensity of the terahertz wave at the time corresponding to the optical delay can be detected by unit 31. THz-TDS uses a sampling method in which the electric field intensities at slightly different times caused by such optical delays are measured to form a single time waveform. A major advantage of THz-TDS is to Fourier transform the time waveform thus obtained into frequency spectra of both the phase and intensity.

In the imaging system 30, a femtosecond laser with a wavelength of 840 nm, an output power of 650 mW, a pulse width of 100 fs or below and a repetition frequency of 80 MHz was used as the femtosecond laser, and a low-temperature grown GaAs (LT-GaAs) film was used for each of the photoconductive switches 32 and 36.

Figure 3:
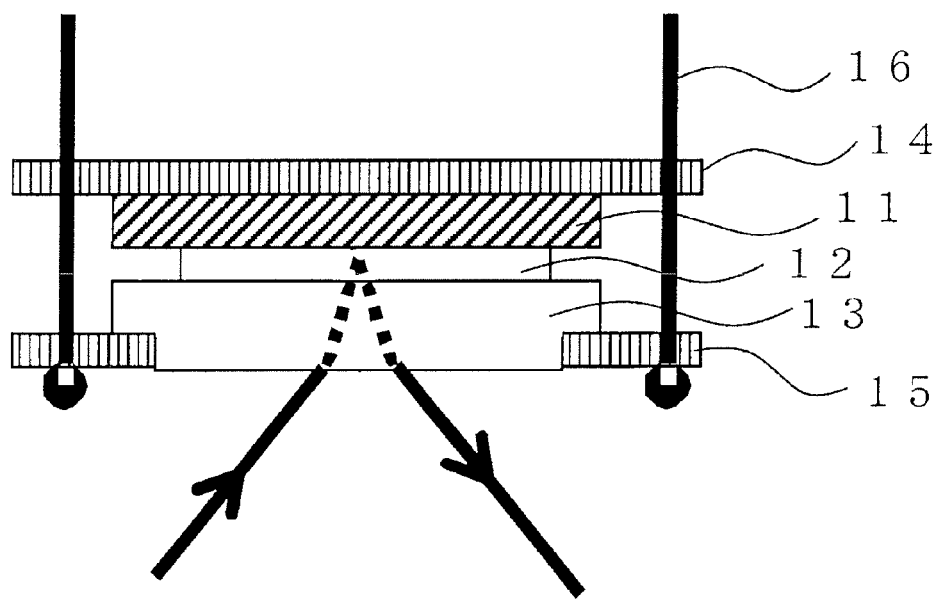
FIG. 3 is a view showing a specific structure of a sample holder in Example 1.

FIG. 3 shows a specific method for fixing the sample 12. The sample 12 is fixed with a reflective member 11 and an entrance member 13 placed on the first principal surface (the top side in FIG. 3) and the second principal surface (the underside in FIG. 3), respectively. Next, the entrance member 13 having a raised bottom surface is fitted at the bottom into an opening of a lower holding plate 15, an upper holding plate 14 is laid over the reflective member 11 put on the sample 12, and these members are fastened by spanner screws 16. At this time, the first and second principal surfaces of the sample 12 are kept parallel to each other and thickness variations of the sample 12 are within ±1%. The arrowed line shows terahertz radiation.

This example has an advantage that since the first and second principal surfaces of the sample 12 are kept parallel to each other, the distance between the first interface 21 and the detecting element 36 and the distance between the second interface 22 and the detecting element can be kept constant, whereby reflected waves from the interfaces, in multi-point measurement through the scanning of the sample in the in-plane direction, can be measured on the same time base.

Measurement is made after a sample chamber (not shown) for accommodating the sample 12 and the laser optical path are subjected to nitrogen purgation in order to eliminate the influence of water vapor.

FIG. 2 shows a schematic view of an optical system of the imaging system 30. Terahertz radiation emitted from the photoconductive switch 32 is reflected by a pair of parabolic mirrors 33 and allowed to enter a focusing point at which the sample 12 is placed. The sample 12 to be measured is put on the XY stage 34 and imaged by sequentially two-dimensionally moving the XY stage 34 while spectrometrically measuring the sample 12 at different points.

In a reflection measurement system in this example, terahertz radiation emitted from the photoconductive switch 32 is collected by the parabolic mirrors 33 (f=237.1 mm, NA=0.26) to enter the sample 12 diagonally at an angle of 20° from below.

In scanning the sample in the in-plane direction by measuring reflected waves from the sample holder 10, it is desired that the sample surface should be smooth and should not have any tilt.

Furthermore, in this example, the entrance member 13 made of high-resistance silicon (Si) single crystal (having a resistivity of 10 kΩcm or more) was placed adjoining one side of the sample. High-resistance silicon (Si) is small in terahertz radiation absorption loss and therefore suitable for the entrance member.

The refractive index of Si in the terahertz wave band is a constant value of 3.415 and greater than those of plastic materials, such as polyethylene. Therefore, the loss of terahertz radiation entering Si from the air is large. However, the absorption coefficient of Si in the terahertz wave band is small, and the loss of terahertz radiation inside Si can be assumed to be approximately zero. Since the entrance member 13 made of a Si material is provided in the sample holder, the terahertz radiation enters the sample 12 at an angle of incidence of 5.8 degrees while being focused on it.

The reflection measurement system in this example detects the reflected wave from the interface between the Si surface and the sample 12. However, the sample to be detected is very small in size and quantity. Therefore, as shown in FIG. 3, a mirror serving as a reflective member 11 is placed on the other side of the sample 12, thereby providing an optical system expecting terahertz radiation absorption of the sample using the round-trip optical path length.

In order to confirm the above effects, two polyethylene plates 12 of different thicknesses were used as samples 12, and comparison was made between their time waveforms and frequency spectra determined by a similar reflection measurement system (a system in which a mirror was placed on the top side of each sample 12).

Figure 4A:
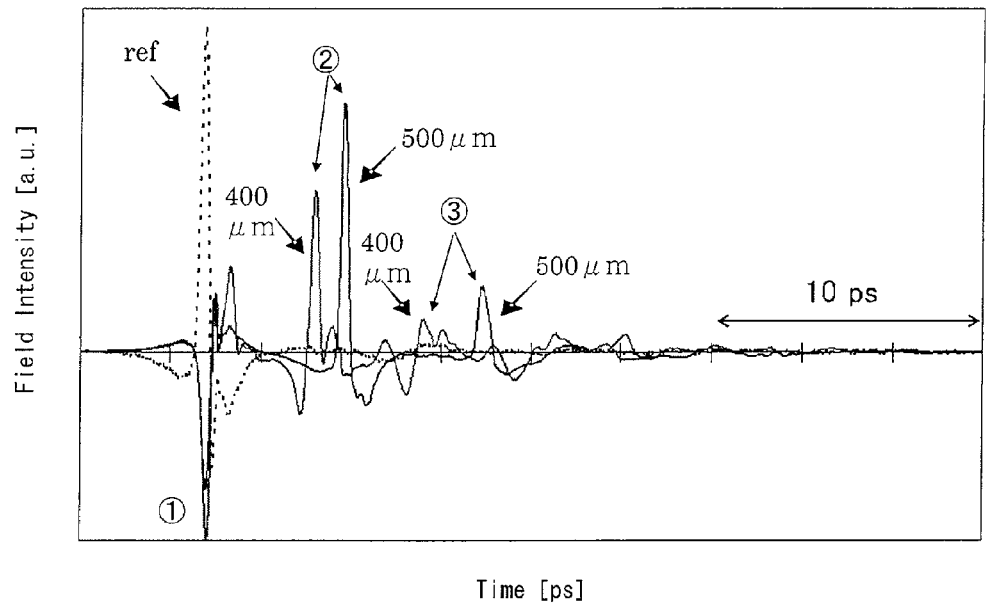
FIG. 4(*a*) is a graph showing time waveforms obtained by a THz-TDS method in Example 1, and FIG. 4(*b*) is a view illustrating the sample holder in Example 1 and terahertz wave propagation paths in the sample holder.
Figure 4B:
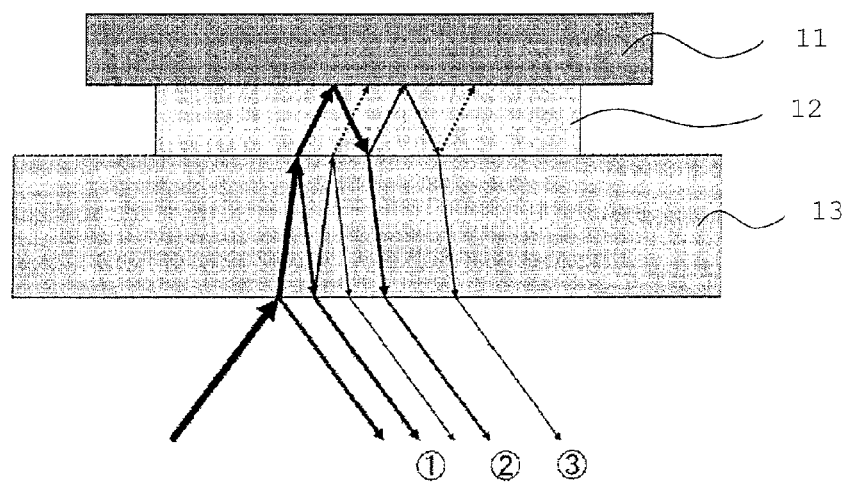
Figure 5:
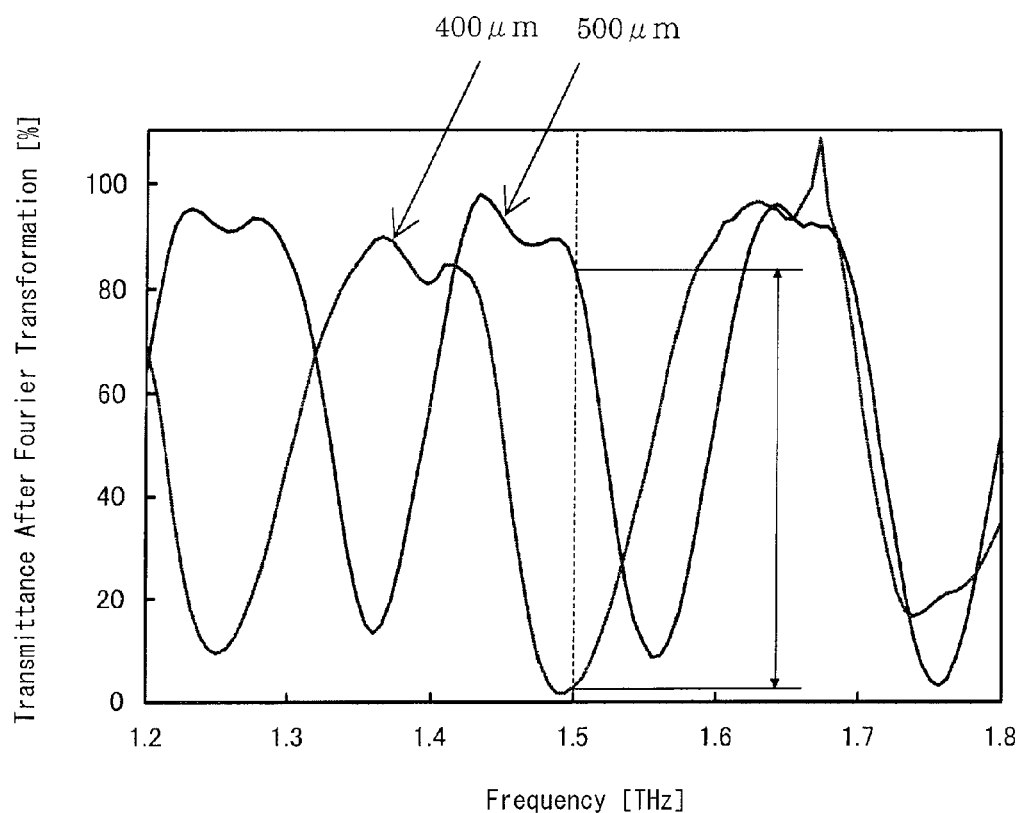
FIG. 5 is a graph showing transmittance versus frequency characteristics in Example 1.

FIG. 4(*a*) shows the time waveforms when the polyethylene plate with a thickness of 500 μm and the polyethylene plate with a thickness of 400 μm were used as samples 12. As shown in FIG. 4(*b*), (i) a reflected signal at the interface between the silicon and the sample, (ii) a reflected signal from the mirror on the top side of the sample and (iii) a reflected signal from the mirror after two round trips were observed in time waveforms. When these results were Fourier transformed and plotted as a function of frequency, the transmittance spectra exhibited interference waves as shown in FIG. 5. These waves are results of interferences due to the above reflected signals (i) and (ii).

The transmittance spectra shown in FIG. 5 were obtained in the following manner. First, three items of data (ref, 400 μm and 500 μm) on time waveform in FIG. 4 were Fourier transformed. Next, the Fourier transform of 400 μm in FIG. 4 was divided by the Fourier transform of ref in FIG. 4, thereby obtaining a transmittance spectrum of 400 μm shown in FIG. 5. Furthermore, the Fourier transform of 500 μm in FIG. 4 was divided by the Fourier transform of ref in FIG. 4, thereby obtaining a transmittance spectrum of 500 μm shown in FIG. 5.

As seen from FIG. 5, it was observed that the interference waves were shifted from each other according to the difference in optical path length between their original waves propagating inside the samples of different thicknesses. As a result, it was observed that two polyethylene plates which were only 100 μm different in thickness from each other exhibited even a 80% transmittance difference at a frequency (1.5 THz) shown in the broken line in FIG. 5.

In such a measurement system, the sample is scanned in the X and Y directions on the XY stage 34 and the scan data is sliced at an arbitrary frequency into an image, whereby the distribution of transmittances or transmission intensities at the frequency can be determined. Besides, the values of physical properties including a refractive index and a dielectric constant can be determined.

EXAMPLE 2

Figure 6A:
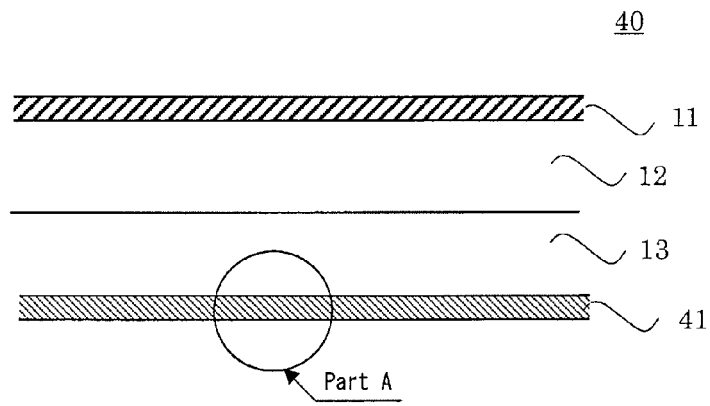
FIG. 6(*a*) is a view showing a sample holder 40 in Example 2, and FIG. 6(*b*) is an enlarged view of Part A in FIG. 6(*a*).
Figure 6B:
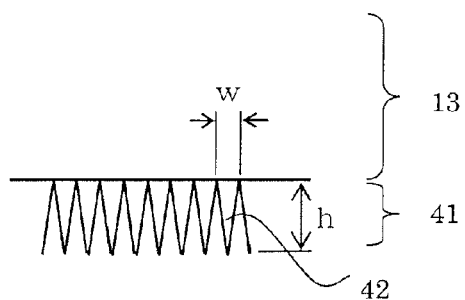

FIG. 6(*a*) shows the sample holder 40 in this example. The sample holder 40 is composed of a reflective member 11, a sample 12, an entrance member 13 and a terahertz radiation reflection suppression layer 41. The elements having the same structure as in Example 1 are identified by the same reference numerals and the description of those parts is not repeated here.

The sample holder 40 is characterized in that an additional layer is provided adjoining and outside (on the atmosphere side) of the entrance member 13. This layer is a terahertz radiation reflection suppression layer 41 for suppressing the reflection of an irradiation beam I.

As described in Example 1, the entrance member 13 is made of a Si material and considerably reflects the irradiation beam I. If reflection occurs immediately after the irradiation, the efficiency of detection of a terahertz wave becomes low, which makes it difficult to measure a very small or a minute amount of sample 12. In addition, the analysis of the form of an interference wave to be obtained becomes complicated. To cope with this, Example 2 is intended to suppress the reflection of the irradiation beam I using the above structure of this example.

FIG. 6(*b*) is an enlarged view of Part A in FIG. 6(*a*). As shown in FIG. 6(*b*), the terahertz radiation reflection suppression layer 41 has a structure in which a plurality of triangular projections 42 having a base w and a height h are arranged at intervals. The triangular projections 42 may be cones or pyramids.

The material of the triangular projections 42 is a Si material identical with that of the entrance member 13. The triangular projections 42 can be formed by etching or grooving a Si substrate.

Since the sample holder 40 has such triangular projections 42, there is produced a condition where the dielectric constant in the surroundings, including the atmosphere, gradually changes. The triangular projections 42 of the terahertz radiation reflection suppression layer 41 provides a smooth transition from the dielectric constant of the atmosphere (approximately 1) to the dielectric constant of silicon (approximately 3.4), resulting in smoothing of the reflection of the irradiation beam I.

It is to be noted that although in Example 2 triangular projections 42 have been illustrated as an example of the terahertz radiation reflection suppression layer, a structure may be employed as another example in which a plurality of layers of different dielectric constants are stacked to stepwise change the dielectric constant. In other words, so long as a layer has a structure in which the dielectric constant gradually changes, it can function as a terahertz radiation reflection suppression layer.

EXAMPLE 3

Figure 7:
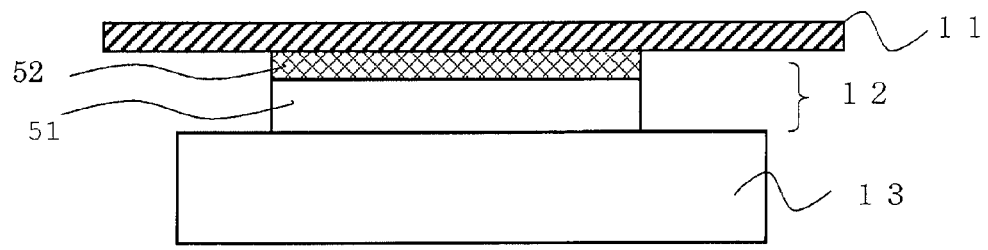
FIG. 7 is a view showing a sample holder in Example 3.

FIG. 7 shows a sample holder 50 composed of a reflective member 11, a sample 12 and an entrance member 13. The elements having the same structure as in Example 1 are identified by the same reference numerals and the description of those parts is not repeated here.

The sample holder 50 is characterized in that the sample 12 is composed of a dielectric substrate 51 and a thin film 52. The sample 12 is formed by sintering a dielectric ceramic material and forming a thin film 52 thereon by a thin-film formation process. Naturally, the dielectric substrate 51 and the thin film 52 have different dielectric constants.

In such a sample 12, a more accurate measurement result can be obtained by changing the vertical orientation of the sample 12 depending on which component should be mainly measured. For example, if the physical properties of the thin film 52 should be mainly measured, the sample 12 only has to be placed with the thin film 52 adjoined to the reflective member 11. On the other hand, if the physical properties of the dielectric substrate 51 should be mainly measured, the sample 12 only has to be placed with the dielectric substrate 51 adjoined to the reflective member 11.

In other words, if the sample 12 is formed of a plurality of layers of different dielectric constants, a more accurate measurement value can be obtained by analyzing the sample 12 with the layer in the plurality of layers in the sample 12 to be analyzed being adjoined to the reflective member 11.

EXAMPLE 4

Example 4 illustrates an example in which a polymer film membrane used for the transfer of proteins or DNAs after being electrophoresed is used to detect binding of a small molecule to a protein. The material of the membrane is polyvinylidene fluoride (PVDF). An example of analysis of a sample in which biomolecules are attached to the membrane is described below.

Because the refractive index of the membrane is as low, approximately 1.1, it can be expected that the adhesion and permeation of the biomolecules thereto should increase the refractive index. Furthermore, this can be expected to reduce the reflection intensity at the interface between the sample and the entrance member (Si) owing to the changed refractive index and increase the effective round-trip optical path length.

Membranes are porous films, and their ability to bind to biomolecules varies according to their material and porosity. Examples of membranes include PVDF and nitrocellulose membranes made by Bio-Rad Laboratories, Inc. and having excellent protein adsorbing ability and membranes made by Millipore Corporation and used as microfiltration filters.

Membranes of various materials exhibit absorption characteristics specific to the terahertz wave band. Therefore, they can be selected according to the intended application. Furthermore, the adsorbing ability specified as the specification of each membrane becomes of less value in analyzing proteins or DNAs, and biomolecules serving as hosts can be selectively adsorbed on the membrane by chemical treatment.

If a liquid sample, such as DNA, is added dropwise onto a substrate, dried and then spectrometrically measured, such as by THz-TDS, uneven drying makes the sample condition nonuniform, which may affect the measurement result. However, it is also known that such a problem can be solved by using a liquid permeable substrate, such as membranes.

Low-molecular compounds themselves do not interact with membranes at all or only extremely weakly interact with them and therefore may easily removed by the rinsing performed after the reaction with proteins.

To cope with this, this example used a method in which a low-molecular compound is imparted hydrophobicity by chemical treatment and immobilized on the membrane by hydrophobic binding to the membrane. The provision of hydrophobicity was implemented by the known technique for binding a hydrophobic polyethylene glycol (PEG) to the low-molecular compound and binding (immobilizing) the low-molecular compound to a PVDF membrane whose surface has hydrophobicity.

It is to be noted that in this example the low-molecular compound was likewise bound to MPEG (methyl polyethylene glycol having an average molecular weight of 5000) different in molecular weight from PEG (an average molecular weight of 3400), and comparison was made between their measurement results different in immobilization process.

The low-molecular compound and protein used in this example were biotin and streptavidin, respectively, which are known to strongly bind together. Biotin was bound to each of PEG and MPEG and immobilized on the membrane by hydrophobic interaction with the membrane. In the immobilization, the concentration of biotin was changed stepwise from $1\times10^{-3}$ M (mol/liter) to $3.2\times10^{-6}$ M, and the biotin was dot blotted, two dots for each concentration, in order to confirm reproducibility. The amount of biotin added dropwise for each dot was 0.2 μL. The added biotin spread in the shape of a circle having a diameter of approximately 3 mm on the membrane.

Thereafter, the membrane was subjected to a blocking treatment with skim milk in order to prevent streptavidin from binding to an untreated membrane. Hereinafter, such a sample produced in this manner is referred to as a membrane array.

In order to confirm the binding of streptavidin, another membrane array produced by performing the same treatment was reacted with streptavidin labeled with a fluorescent labeling agent "Alexa Fluor (registered trademark) 633" and the confirmation of binding was implemented by a separate fluorescence detection.

Figure 8:
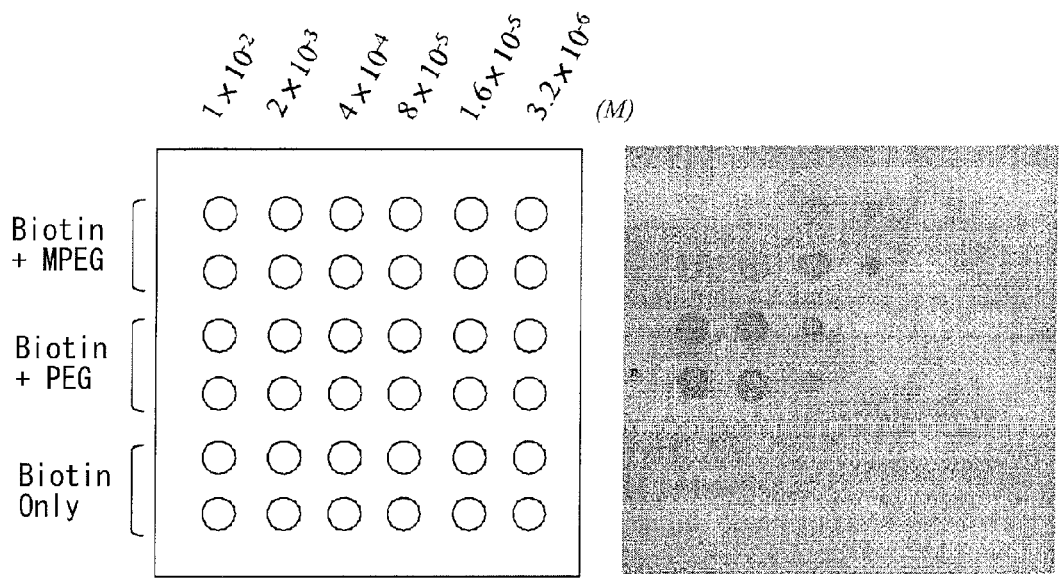
FIG. 8 shows a schematic diagram of a biotin membrane array in Example 4 and a fluorescently detected image as a comparative example.

FIG. 8 shows a schematic view of a membrane array produced in the above manner and a result of detection using the fluorescent label. In a fluorescent image shown in the right part of FIG. 8, dark regions are regions in which labeled streptavidin has been detected.

In the membrane array, the lower two rows, in which only a biotin solution was added dropwise without immobilizing biotin on the membrane, could not be bound to streptavidin because the biotin was rinsed away from the membrane during the rinsing process. From this, it was confirmed that the immobilization of biotin with PEG could properly be achieved and immobilized biotin had an ability to bind to streptavidin.

Figure 9:
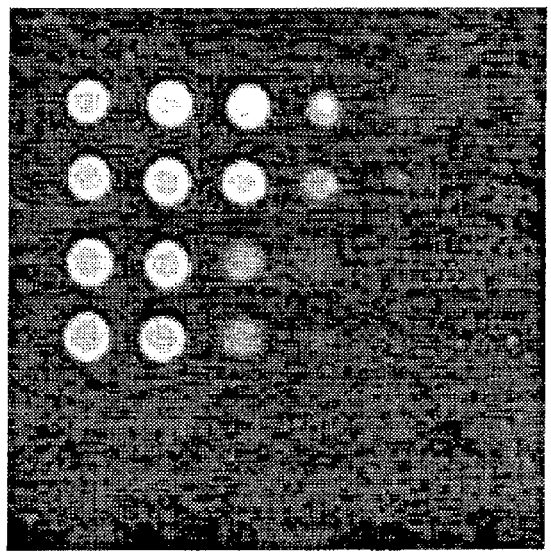
FIG. 9 is a detected image of streptavidin on a biotin membrane array in Example 4.

FIG. 9 shows an image of sample analysis at a frequency of 1.5 THz obtained by the THz-TDS reflection measurement system. This image is a result of non-label detection in which non-labeled streptavidin was reacted with a membrane array and shows that the brighter the dot, the higher the degree of adsorption of streptavidin. Like the fluorescent image, the existence of streptavidin could not be found in the lower two rows in which only a biotin solution was added dropwise.

Furthermore, the reactivity of dots in which biotin was immobilized on the membrane using MPEG was higher. This result has the same tendency as the result using the fluorescence detection method.

Various materials acting as linkers in the above manner have been reported. There are various optimal linking techniques according to the type of small molecule and the type of membrane.

Furthermore, absorption, although it was slight, could be observed even at a lower concentration ($1.6\times10^{-5}$ M) than could not been found in the fluorescent image. Thus, the THz-TDS method could detect to a smaller amount than the fluorescence detection using "Alexa Fluor 633".

EXAMPLE 5

Figure 10:
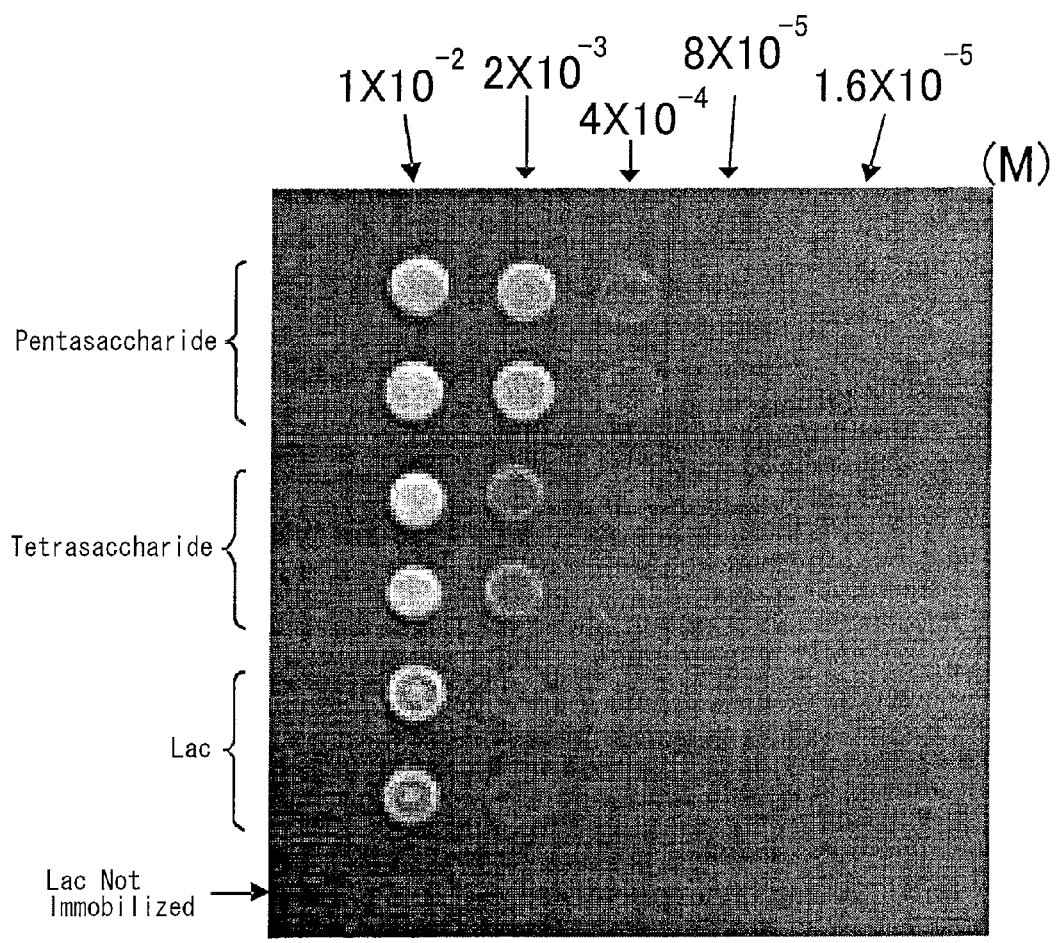
FIG. 10 is a detected image of lectin on a sugar chain membrane array in Example 5.

In Example 5, other biomolecules were subjected to non-label detection using the present invention, and the presence or absence of binding between carbohydrate and glycoprotein (lectin) was imaged. The image is shown in FIG. 10.

Sugar chains are compounds in which a plurality of sugars are linked. In particular, sugar chains existing on a cell surface bind to lectin, virus or lipid to transfer information to the cell. Sugar chains are said to be essential substances also for life action because they are closely related to cell growth, infection, immune system and the like. However, it has been considered that the interaction of sugar chains is difficult to analyze because their force of binding to lectin or the like is not as high as those to antigens or antibodies.

In this example, the reactions of sugar chains with lectin, which exhibits a selective bindability to galactose in sugar chains, were imaged in the same manner as in the above examples and subjected to non-label detection. The sugar chains used were tetrasaccharide, pentasaccharide and lactose (Lac) at different concentrations and immobilized, vertically arranged two dots for each sugar chain at each concentration, on the membrane. In addition, dots of lactose not subjected to the immobilization treatment were arranged in the lowest row of the membrane array.

The results confirmed that, like the membrane array of biotin as described above, the dots of lactose not immobilized were peeled off from the membrane by a treatment, such as rinsing, and could not be reacted with lectin.

It can be considered reasonable that pentasaccharide and tetrasaccharide exhibited higher reactivities with lectin than lactose, because pentasaccharide and tetrasaccharide contain two galactose units per molecule and lactose contains a single galactose unit per molecule.

A non-label detection using a membrane array of low-molecular compound, which has been developed from the present technique, can be expected to be a screening technique that can rapidly search candidate substances in the field of drug discovery.

In introducing the present technique into screening, an array of known candidate substances is reacted with unknown protein groups (mixtures) and the reaction result is imaged. If binding is observed, apart of the binding portion can be excised and its molecular weight can be determined using electrophoresis. Furthermore, another part excised from the binding portion can be crystallized and examined in terms of steric structure using X-ray structural analysis. This technique is suitable for analysis of substances difficult to subject to conventional labeling techniques and analysis of protein groups in mixture form extracted from a biological body. For example, this technique can suitably be used for Aβ protein because of its high agreeability.

Reference Signs List
- 10 sample holder
- 11 reflective member
- 12 sample
- 13 entrance member
- 21 first interface
- 22 second interface
- 23 third interface
- 31 laser light source
- 32 photoconductive switch (generating element)
- 33, 35 parabolic mirror
- 34 XY stage
- 36 photoconductive switch (detecting element)
- 37 data processing section
- I irradiation beam
- $t_0, t_1, t_2, t_3, r_1t_1, r_2t_1$ intra-entrance member propagating wave
- $r_0, r_1, r_2, r_3, t_2r_0$ intra-sample propagating wave
- $R_1, R_2, R_3$ outgoing wave
- $R_0$ reflected wave

The invention claimed is:

1. A sample analysis method for analyzing a sample having a permeability to terahertz radiation, the method comprising:
   providing a reflective member adjoining a first principal surface of a sample, wherein the reflective member is a mirror;
   providing an entrance member having first and second surfaces, the first entrance member surface adjoining a second principal surface of the sample and the second entrance member surface being remote from the second principal surface of the sample;
   delivering terahertz radiation from outside of the entrance member towards the sample; and
   analyzing an interference wave generated from a first-surface reflected wave at the interface between the first principal surface of the sample and the reflective member and a second-surface reflected wave at the interface between the second principal surface of the sample and the entrance member.

2. The sample analysis method according to claim 1, wherein the interface between the first principal surface of the sample and the reflective member and the interface between the second principal surface of the sample and the entrance member are parallel to each other.

3. The sample analysis method according to claim 2, wherein the interference wave is generated from a wave emitted from the entrance member after the first-surface reflected wave passes through the sample and the entrance member, and a wave emitted from the entrance member after the second-surface reflected wave passes through the entrance member.

4. The sample analysis method according to claim 3, wherein the interference wave is generated from a wave from multiple reflections of a terahertz wave at the interface between the first principal surface of the sample and a wave from multiple reflections of a terahertz wave at the interface between the second principal surface of the sample and the entrance member.

5. The sample analysis method according to of claim 4, wherein the refractive index of the reflective member is greater than that of the sample, the refractive index of the entrance member is greater than that of the sample, and the refractive index of the entrance member is greater than that of the air present outside the entrance member.

6. The sample analysis method according to claim 5, wherein a terahertz radiation reflection suppression layer is provided adjoining the second surface of the entrance member.

7. The sample analysis method according to claim 5, wherein the sample is formed of a plurality of layers having different dielectric constants, and the layer to be analyzed is adjoined to the reflective member.

8. The sample analysis method according to claim 1, wherein the interference wave is generated from a wave emitted from the entrance member after the first-surface reflected wave passes through the sample and the entrance member, and a wave emitted from the entrance member after the second-surface reflected wave passes through the entrance member.

9. The sample analysis method according to claim 1, wherein the interference wave is generated from a wave from multiple reflections of a terahertz wave at the interface between the first principal surface of the sample and a wave from multiple reflections of a terahertz wave at the interface between the second principal surface of the sample and the entrance member.

10. The sample analysis method according to of claim 1, wherein the refractive index of the reflective member is greater than that of the sample, the refractive index of the entrance member is greater than that of the sample, and the refractive index of the entrance member is greater than that of the air present outside the entrance member.

11. The sample analysis method according to claim 1, wherein a terahertz radiation reflection suppression layer is provided adjoining the second surface of the entrance member.

12. The sample analysis method according to claim 1, wherein the sample is formed of a plurality of layers having different dielectric constants, and the layer to be analyzed is adjoined to the reflective member.

13. A sample analysis method for analyzing a sample having a permeability to terahertz radiation, the method comprising:
   providing a reflective member adjoining a first principal surface of a sample, wherein the reflective member is a mirror;
   providing an entrance member having first and second surfaces, the first entrance member surface adjoining a second principal surface of the sample and the second entrance member surface being remote from the second principal surface of the sample;

delivering terahertz radiation from the second surface of the entrance member towards the sample, thereby generating a reflected wave at the interface between the first principal surface of the sample and the reflective member, a reflected wave at the interface between the second principal surface of the sample and the entrance member, and a reflected wave at the interface between the entrance member and the second surface of the entrance member; and then analyzing the sample using an interference wave generated from a plurality of outgoing waves emitted out from the entrance member away from the sample.

14. The sample analysis method according to of claim 13, wherein the refractive index of the reflective member is greater than that of the sample, the refractive index of the entrance member is greater than that of the sample, and the refractive index of the entrance member is greater than that of the air present outside the entrance member.

15. The sample analysis method according to claim 14, wherein a terahertz radiation reflection suppression layer is provided adjoining the second surface of the entrance member.

16. The sample analysis method according to claim 14, wherein the sample is formed of a plurality of layers having different dielectric constants, and the layer to be analyzed is adjoined to the reflective member.

* * * * *

UNITED STATES PATENT AND TRADEMARK OFFICE
CERTIFICATE OF CORRECTION

| | |
|---|---|
| PATENT NO. | : 8,514,403 B2 |
| APPLICATION NO. | : 13/086759 |
| DATED | : August 20, 2013 |
| INVENTOR(S) | : Yuichi Ogawa et al. |

Page 1 of 1

It is certified that error appears in the above-identified patent and that said Letters Patent is hereby corrected as shown below:

On the Title Page
    Item 30 Foreign Application Priority Data please delete "Oct. 24, 2008" and replace with *Oct. 14, 2008*

Signed and Sealed this
Tenth Day of December, 2013

Margaret A. Focarino
*Commissioner for Patents of the United States Patent and Trademark Office*